(12) United States Patent
Gildersleeve et al.

(10) Patent No.: US 12,349,932 B2
(45) Date of Patent: Jul. 8, 2025

(54) CONTROL MECHANISM FOR END EFFECTORS AND METHOD OF USE

(71) Applicant: Boston Scientific Scimed, Inc., Maple Grove, MN (US)

(72) Inventors: Kathryn Gildersleeve, Maple Grove, MN (US); Ramon Estevez, Lowell, MA (US); Christopher R. Deuel, Melrose, MA (US); Barry Weitzner, Acton, MA (US); Maggie Burds, Peosta, IA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 644 days.

(21) Appl. No.: 17/646,049

(22) Filed: Dec. 27, 2021

(65) Prior Publication Data

US 2022/0202433 A1    Jun. 30, 2022

Related U.S. Application Data

(60) Provisional application No. 63/131,189, filed on Dec. 28, 2020.

(51) Int. Cl.
*A61B 17/29*    (2006.01)

(52) U.S. Cl.
CPC ...... *A61B 17/29* (2013.01); *A61B 2017/2903* (2013.01); *A61B 2017/2936* (2013.01); *A61B 2017/2939* (2013.01)

(58) Field of Classification Search
CPC ............ A61B 17/29; A61B 2017/2903; A61B 2017/2936; A61B 2017/2939; A61B 2017/2927; A61B 1/0014; A61B 1/018; A61B 2017/00296; A61B 17/32; A61B 17/320016; A61B 17/3201; A61B 17/3205; A61B 17/3211; A61B 17/068–2017/07285
See application file for complete search history.

(56) References Cited

U.S. PATENT DOCUMENTS

| | | | |
|---|---|---|---|
| 2005/0234297 A1* | 10/2005 | Devierre | A61B 1/00087 600/129 |
| 2016/0029875 A1* | 2/2016 | Okada | A61B 1/00101 600/107 |
| 2020/0054320 A1 | 2/2020 | Harris et al. | |
| 2020/0275925 A1 | 9/2020 | Smith et al. | |
| 2020/0367921 A1 | 11/2020 | Basu et al. | |

\* cited by examiner

*Primary Examiner* — Kathleen S Holwerda
(74) *Attorney, Agent, or Firm* — Bookoff McAndrews PLLC

(57) ABSTRACT

A medical device includes a shaft including a longitudinal axis, an end effector connected to a distal end of the shaft to move from a first orientation, where a longitudinal axis of the end effector is approximately parallel to the longitudinal axis of the shaft, to a second orientation, where an angle is formed between the longitudinal axis of the end effector and the longitudinal axis of the shaft, and an elongated member attached to a proximal end of the end effector, wherein manipulation of the elongated member moves the end effector between the first orientation and the second orientation.

9 Claims, 11 Drawing Sheets

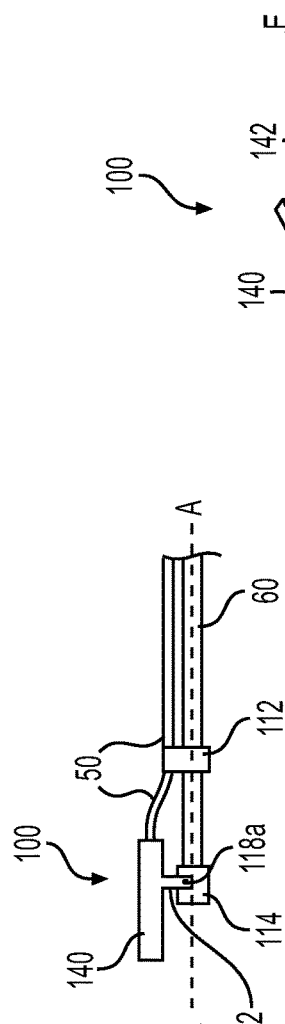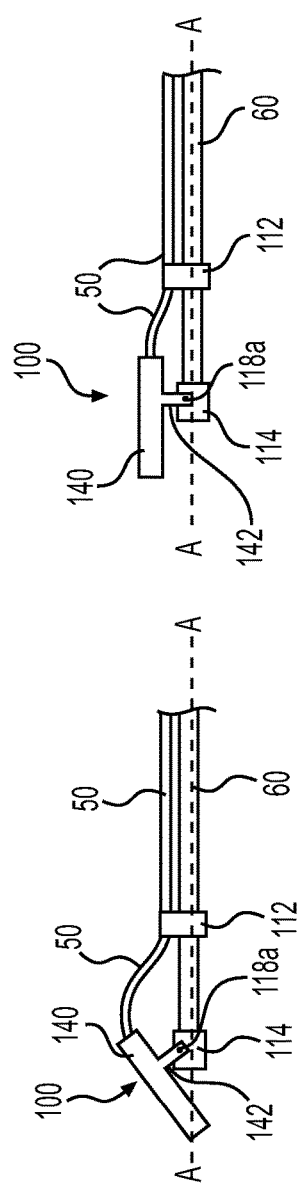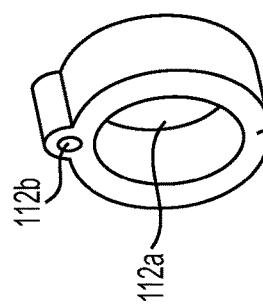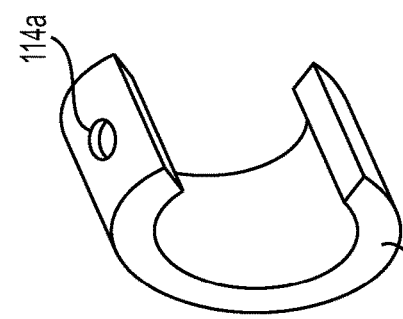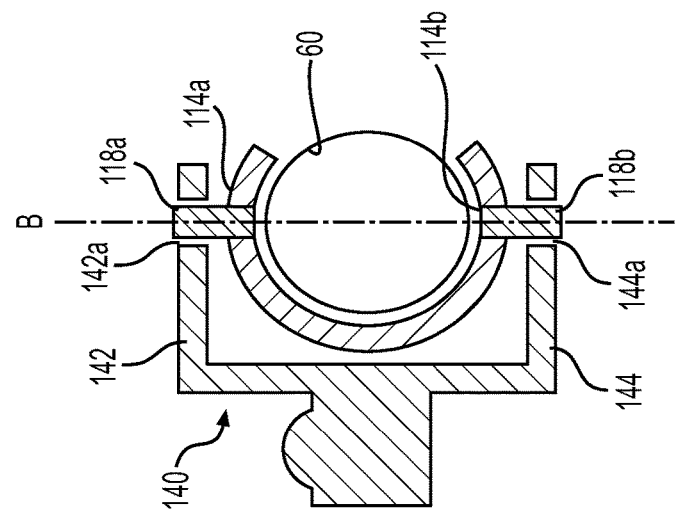

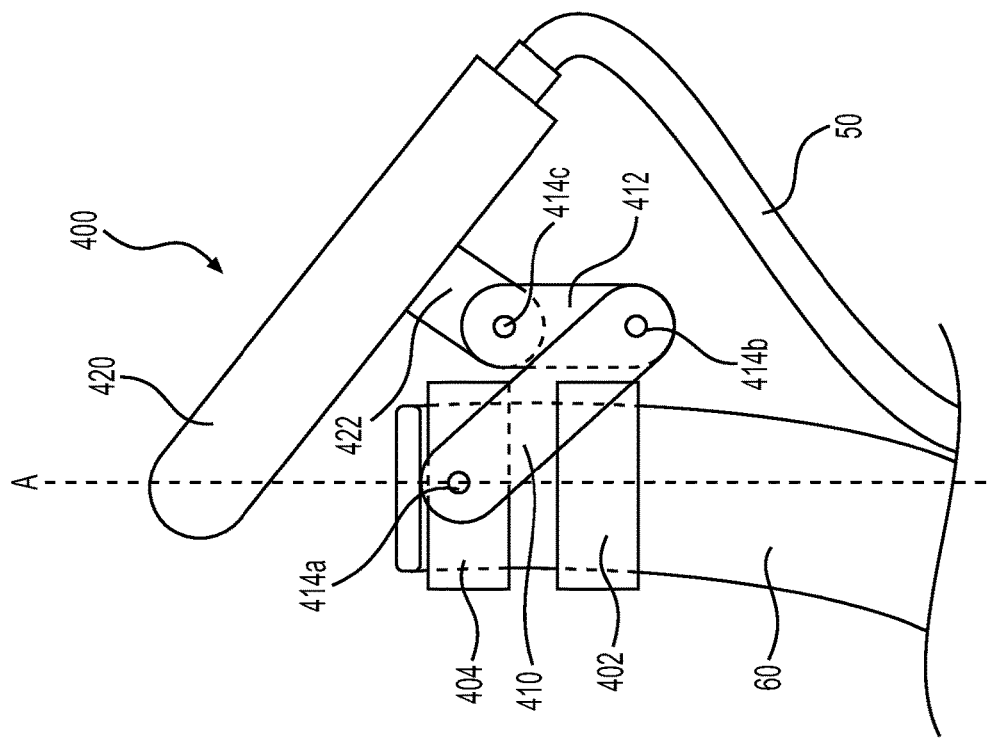
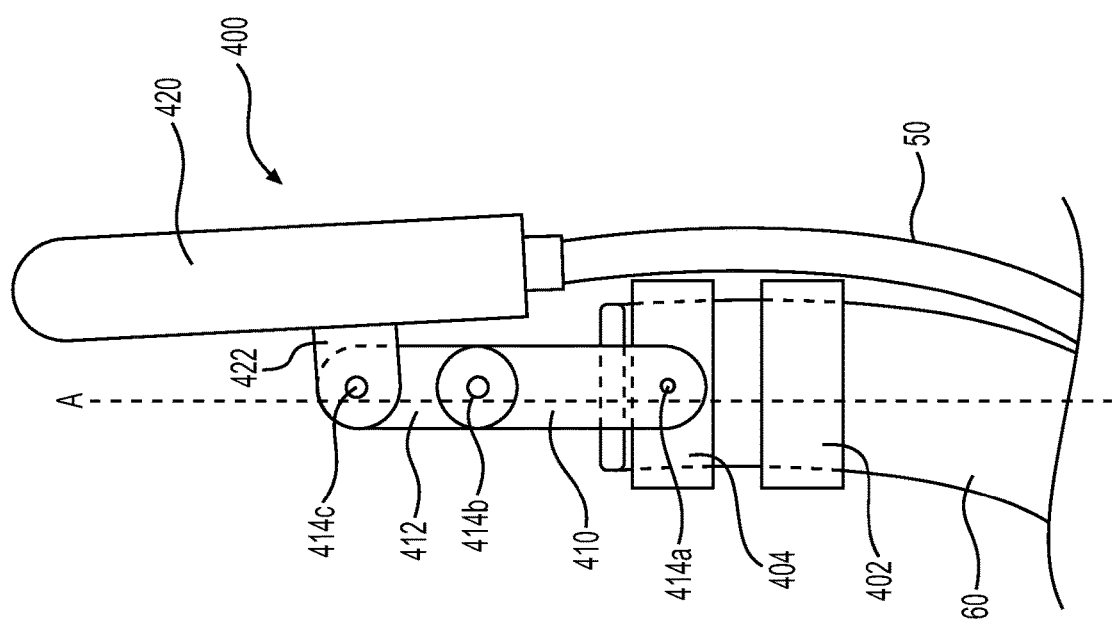
FIG. 4B
FIG. 4A

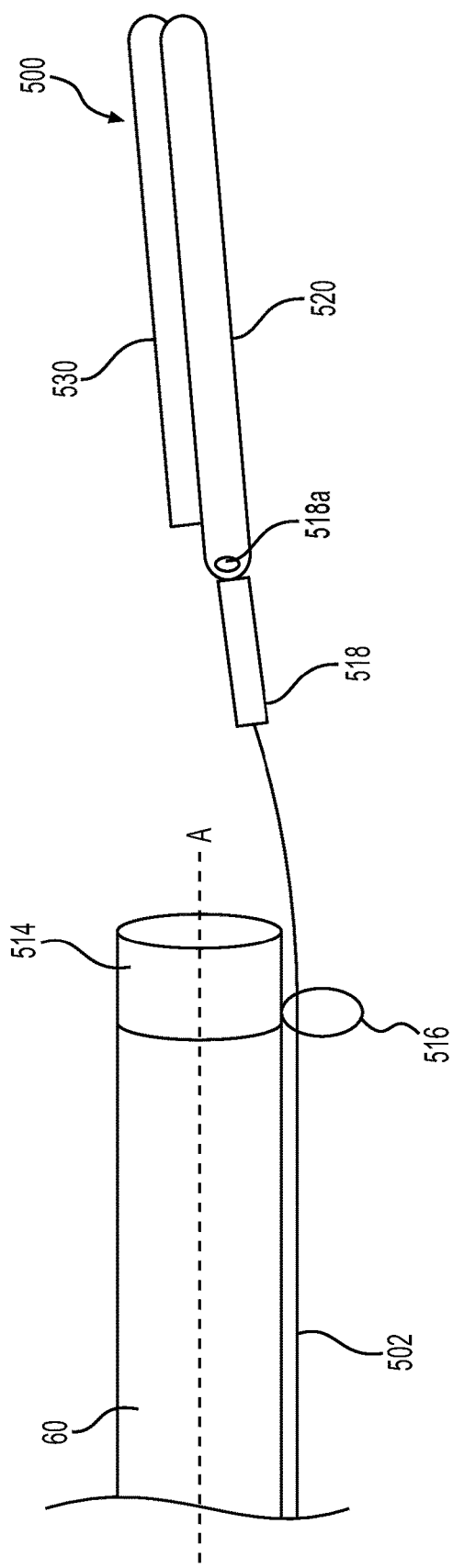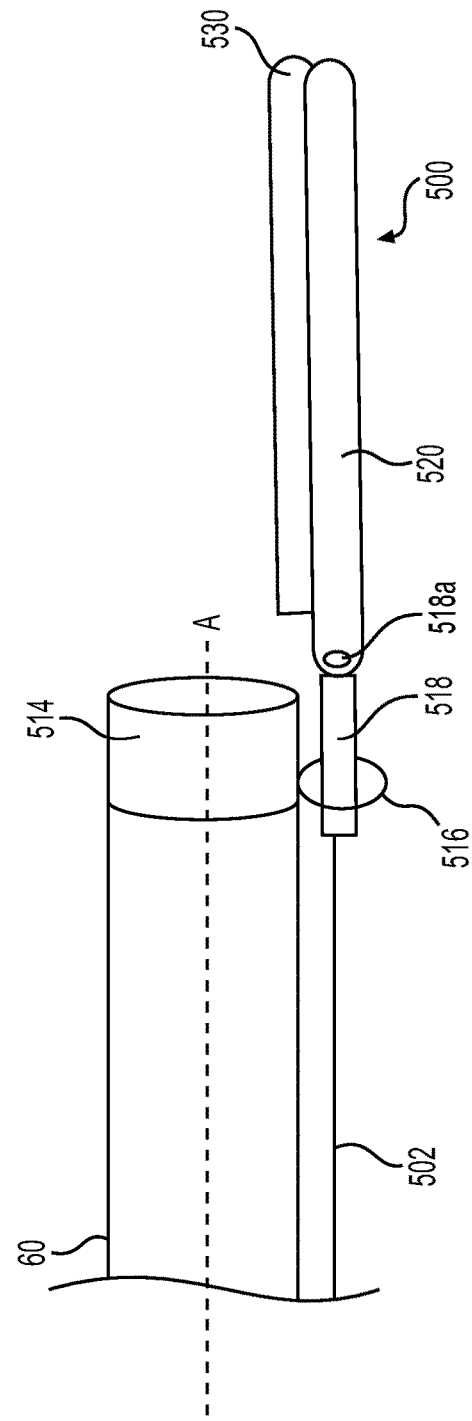
FIG. 5A
FIG. 5B

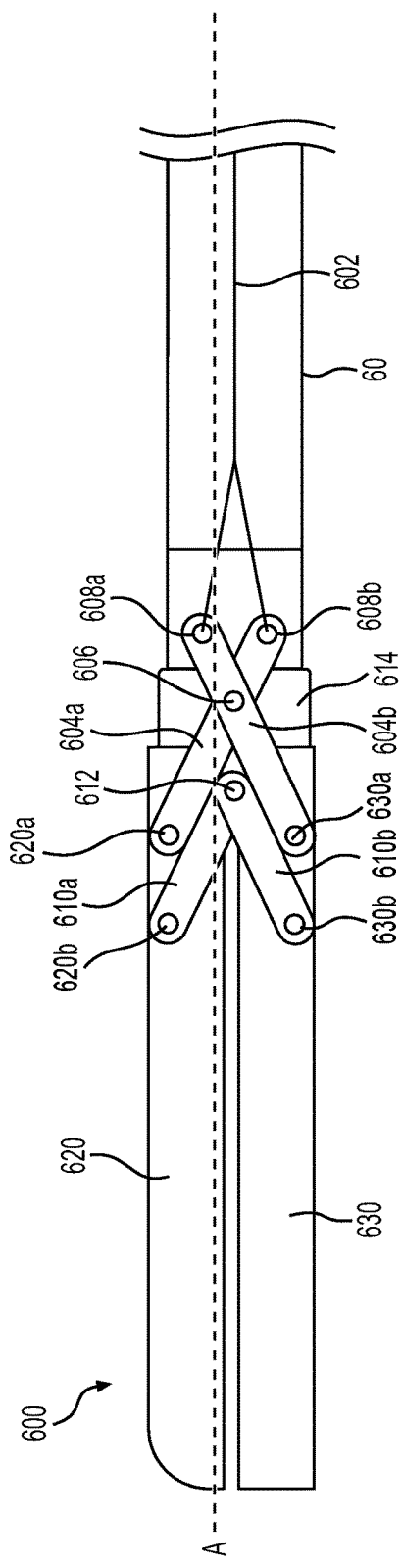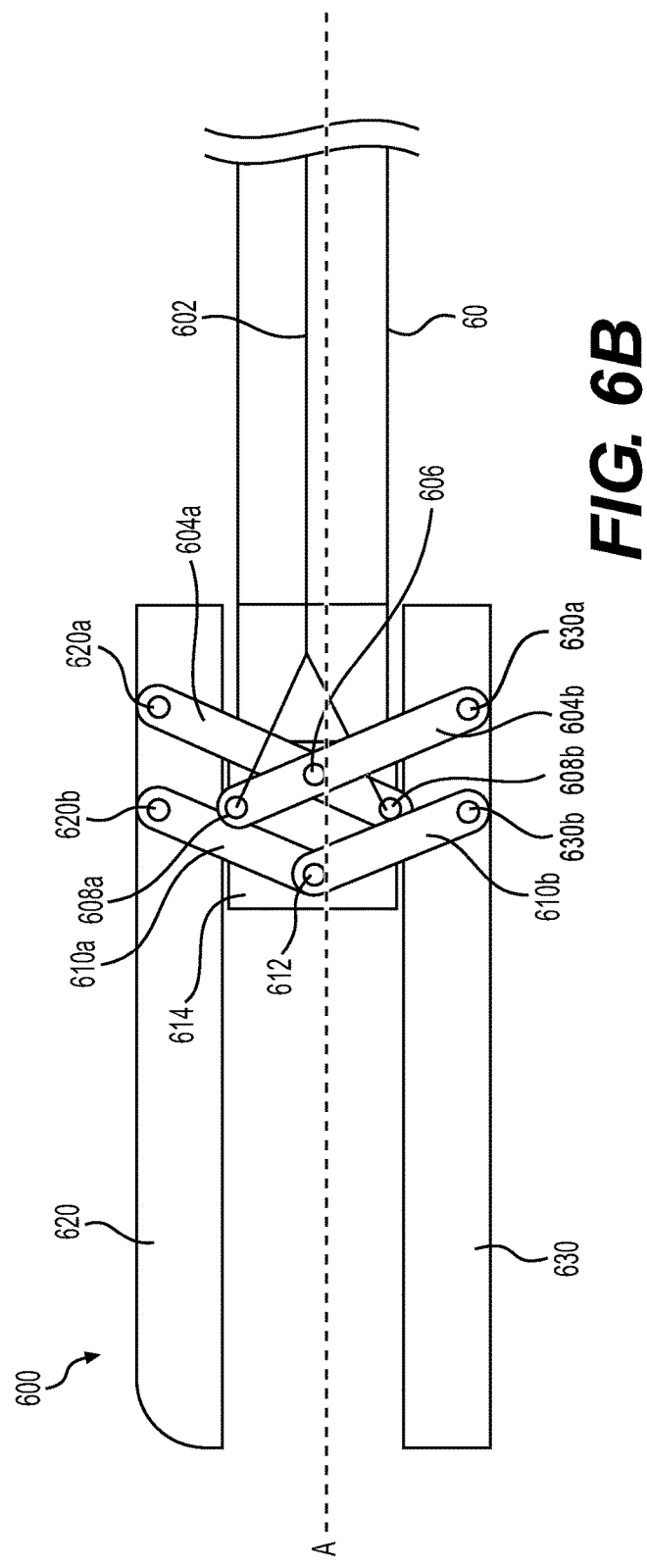

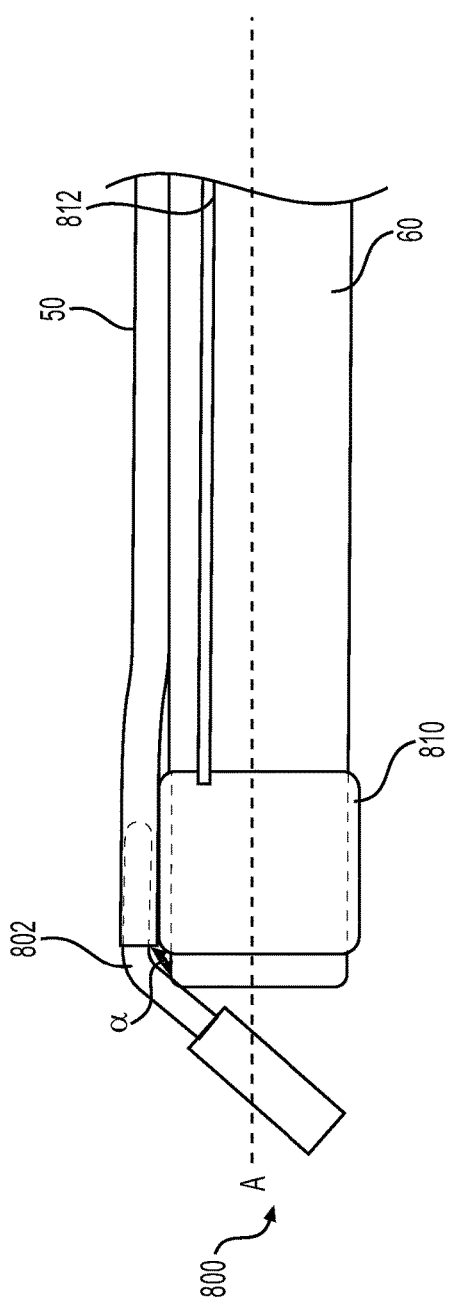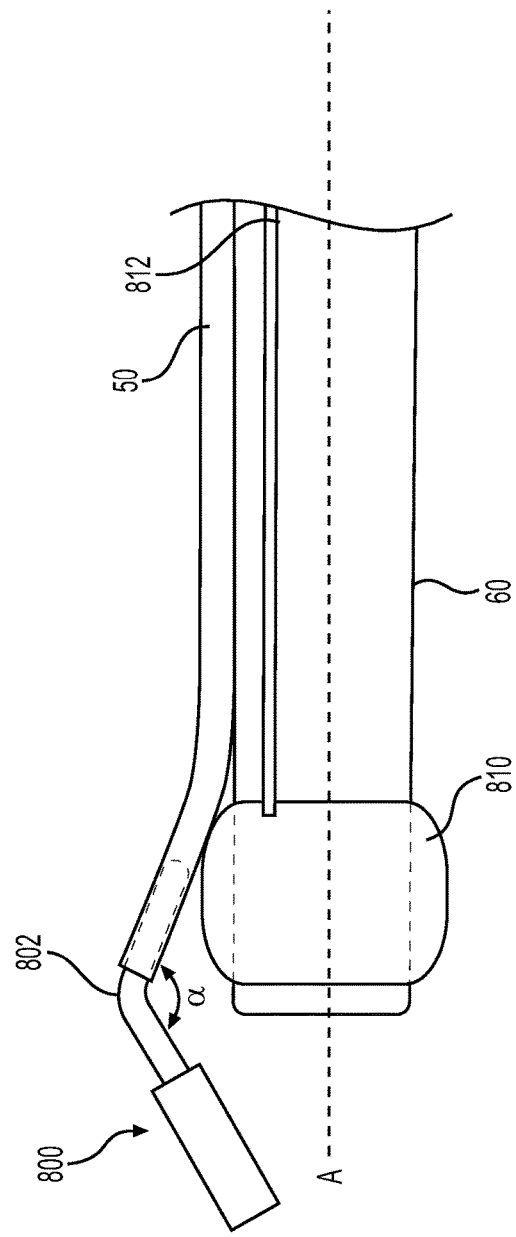

CONTROL MECHANISM FOR END EFFECTORS AND METHOD OF USE

CROSS-REFERENCE TO RELATED APPLICATIONS

This application claims the benefit of priority of U.S. Provisional Patent Application No. 63/131,189, filed Dec. 28, 2020, the entirety of which is incorporated herein by reference.

TECHNICAL FIELD

This disclosure relates to minimally invasive (e.g., endoscopic and/or laparoscopic) medical devices and related methods of use. In embodiments, the disclosure relates to one or more control mechanisms for end effectors, e.g., tissue fastening devices such as stapler devices, and related methods of use, among other aspects.

BACKGROUND

Technological developments have given users of medical systems, devices, and methods, the ability to conduct increasingly complex procedures on subjects. The coupling of tissue in, for example, a subject's gastrointestinal tract or other locations within the body, is a type of procedure in which difficulties may arise. Surgical devices that grasp or clamp tissue between opposing jaw structures and then join, otherwise secure together, the tissue by surgical fasteners provide many benefits. The fasteners may include surgical staples. In some procedures, a cutting instrument may be provided to cut the tissue which has been joined by the fasteners. Drawbacks of these systems may include, for example, access to target sites via tortuous paths and/or paths having small cross-sectional diameters. This may result in tissue not being properly accessed at target sites to staple and/or cut tissue using scopes, which may increase therapy time and/or cost, and/or result in trauma to the patient (e.g., if more invasive procedures are required to access the target site). This disclosure may solve one or more of these problems or other problems in the art. The scope of the disclosure, however, is defined by the attached claims and not the ability to solve a specific problem.

SUMMARY OF THE DISCLOSURE

According to an aspect, a medical device includes a shaft including a longitudinal axis, an end effector connected to a distal end of the shaft and configured to move from a first orientation, where a longitudinal axis of the end effector is approximately parallel to the longitudinal axis of the shaft, to a second orientation, where an angle is formed between the longitudinal axis of the end effector and the longitudinal axis of the shaft, and an elongated member attached to a proximal end of the end effector, wherein manipulation of the elongated member is configured to move the end effector between the first orientation and the second orientation.

The medical device may include a first fixation device which may be connected to a distal end of the shaft, and a second fixation device which may be connected to the shaft proximal of the first fixation device, wherein the end effector may be pivotally coupled to the first fixation device.

The end effector may be connected to the first fixation device via a pair of pins, and wherein the pins may define a pivot axis about which the end effector may be configured to rotate.

The end effector may include a U-shaped body portion configured to receive a medical tool.

The medical device may further include an arm pivotally connected to the distal end of the shaft about a pivotal axis, wherein the end effector may be pivotally connected to a distal end of the arm.

The medical device may further comprise a device configured to restrict movement of the arm about the pivotal axis.

The medical device may further include one or more of a protrusion extending from a surface of the shaft or a fluid container configured to receive fluid.

The device may include the protrusion, and wherein the arm may be configured to move from the first position to the second position when a force sufficient to overcome a friction force of the protrusion is applied to the elongated member.

The arm may be configured to move from a first position, in which the end effector may be locked in the first orientation, to a second position, in which the arm may be capable of moving from the first orientation to the second orientation.

The arm may include a first link pivotally connected to a second link, wherein a distal end of the first link may be pivotally connected to the end effector, wherein a proximal end of the second link may be pivotally connected to the distal end of the shaft, wherein the first link and the second link are approximately parallel to the longitudinal axis of the shaft when the end effector may be in the first orientation, and at least one of the first link or the second link may be angled relative to the longitudinal axis of the shaft when the end effector may be in the second orientation.

Movement of the elongated member in the distal direction may be configured to move the end effector from the first orientation to the second orientation.

The medical device may further comprise an arm extending from the shaft in a distal direction, and wherein the end effector may be pivotally connected to the arm.

The arm may include a fluid container at a proximal end, wherein the fluid container may include a plurality of baffles configured to allow the fluid container to expand and contract.

The arm may be configured to extend in the distal direction when a fluid is supplied to the fluid container.

The end effector may be locked in the first orientation when fluid is removed from the fluid container.

According to another aspect, a medical device includes a shaft including a longitudinal axis, an end effector attached to a distal end of the shaft and configured to move from a first orientation, where a longitudinal axis of the end effector is approximately parallel to the longitudinal axis of the shaft, to a second orientation, where an angle is formed between the longitudinal axis of the end effector and the longitudinal axis of the shaft, and a fluid container configured to receive fluid, wherein the end effector is capable of being moved from the first orientation to the second orientation when fluid is supplied to the fluid container, and wherein the end effector is capable of being moved from the second orientation to the first orientation when fluid is removed from the fluid container.

The medical device may further include an elongated member extending from a distal end of the end effector, and wherein the end effector may be configured to move from the first orientation to the second orientation based on a distal movement of the elongated member.

The fluid container may include a plurality of baffles, wherein supplying fluid to the fluid container may be configured to move a distalmost end of the fluid container in a distal direction, and wherein removing fluid from the fluid container may be configured to move the distalmost end of the fluid container in a proximal direction.

According to yet another aspect, a medical method includes advancing an end effector of a medical device to a target site within a patient, wherein the end effector is positioned in a first orientation such that a longitudinal axis of the end effector is parallel to a longitudinal axis of a shaft of the medical device, moving an elongate member connected to the end effector in a distal direction to cause the end effector to move from the first orientation to a second orientation, wherein the end effector is angled relative to a longitudinal axis of the shaft in the second orientation, and actuating a control mechanism to cause a first jaw to pivot relative to a second jaw and perform a procedure at the target site.

The method may further include rotating the end effector from the second orientation to the first orientation, and removing the end effector from the patient.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 1B, 1C, 1D, 1E, 1F, and 1G are perspective views of the end effector of FIG. 1A and attachment mechanisms for the end effector, according to an embodiment;

FIGS. 4A and 4B are side views of another exemplary end effector, according to an embodiment;

FIGS. 5A and 5B are side views of a further exemplary end effector, according to an embodiment;

FIGS. 6A and 6B are side views of yet another exemplary end effector, according to an embodiment;

FIGS. 8A, 8B, 8C, and 8D are side views of another exemplary end effector, according to an embodiment;

DETAILED DESCRIPTION

Figure 1A:
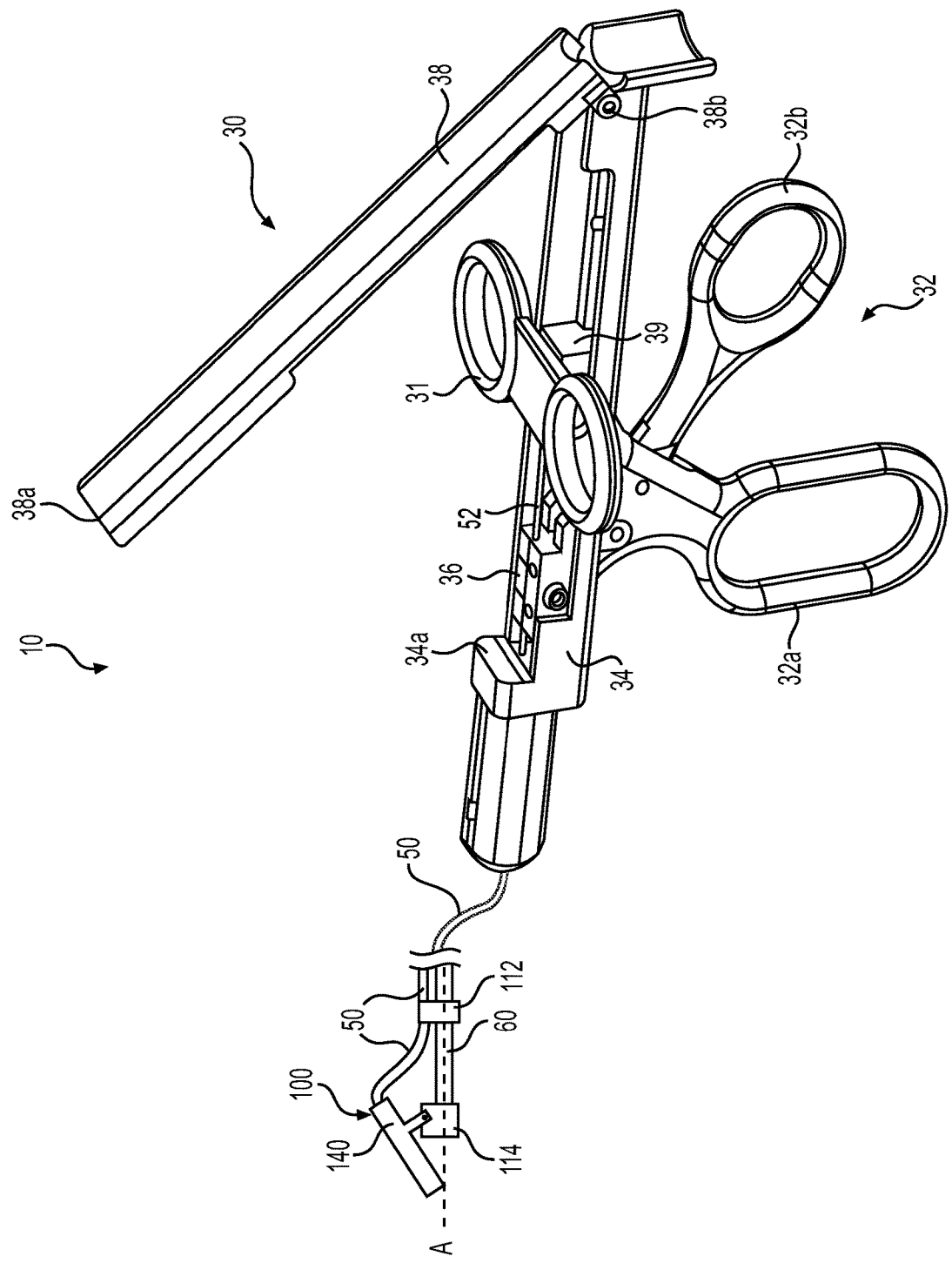
FIG. 1A is a schematic view of a medical device including an end effector, according to an embodiment.

This disclosure is described with reference to exemplary medical systems and medical tools for accessing a target site, for example, for grasping, cutting, and/or stapling tissue, and providing a control mechanism for controlling an orientation of an end effector relative to the medical tools. This may provide improved medical tool functionality and/or may assist medical professionals with improved access to target sites, which may improve cutting and/or fastening of tissue. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. This disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Additionally, terms that indicate the geometric shape of a component/surface refer to both exact and approximate shapes.

Embodiments of this disclosure may be used to fasten tissue in an endo-luminal space, or facilitate the process thereof. According to an example, the fastening device may be a tissue stapling apparatus, which may include a resection or cutting mechanism (e.g., an integrated knife) and a stapling mechanism (e.g., a stapler). The fastening device may be delivered through an endoscope working channel to the target tissue site. Alternatively, the fastening device may be attached to a distal end of the endoscope. All or parts of the fastening device could be metallic (such as stainless steel, titanium, or cobalt chrome), plastic (such as polyetheretherketone (PEEK) or the like), or include a shape memory metal (such as Nitinol), a shape memory polymer, a polymer, or any combination of materials. While reference is made herein to a fastening device with a control mechanism for controlling an orientation of the fastening device, the described control mechanism may be used with any set of jaws or other end effectors pivotally connected together at a distal end of a catheter, sheath, tube, or the like. The control mechanism may enable pivotal movement of the end effector about one or more pivot points at the distal end of the endoscope, which may provide improved grasping of tissues. For example, the control mechanism may enable the end effector to be arranged parallel to a longitudinal axis of the endoscope during insertion of the end effector to the target site, and may enable the end effector to rotate about one or more pivot points to grasp tissue once the end effector is at the target site. In this manner, the end effector and the endoscope may navigate tortuous pathways within the body.

FIG. 1A shows an apparatus 10 in accordance with an example of this disclosure. Apparatus 10 may include a scope (e.g., a colonoscope, endoscope, duodenoscope, or the like) for imaging, providing light to a target site, and/or for introducing instruments to the target site, and a surgical stapling apparatus configured to engage body tissue, and apply a plurality of fasteners thereto during minimally invasive procedures, such as those procedures using the scope. In some embodiments apparatus 10 may include a suturing apparatus to deliver a suture for tissue closure during minimally invasive surgical procedures. Apparatus 10 may be used to apply a suture, clips, or other fasteners, but will be primarily discussed in the context of grasping tissue in preparation of performing additional procedures to the tissue, e.g., stapling and/or cutting the tissue.

As illustrated in FIG. 1A, the grasping or stapling device of apparatus 10 may include a handle assembly 30 at a proximal end, an end effector 100 at a distal end, and an elongated body 50 (e.g., a shaft, a catheter, or the like) connecting a distal end of handle assembly 30 to a proximal end of end effector 100. Elongated body 50 may extend any length suitable for endoscopic or laparoscopic procedures. In some instances, elongated body 50 may be configured to be positioned within a working channel of an endoscope. Alternatively, elongated body 50 may extend along an outer surface of the endoscope if, for example, the endoscope includes only a single lumen and/or a diameter of the lumen(s) of the endoscope are too small to receive elongated body 50. In some instances, elongated body 50 and end effector 100 are located on the outer surface of the endoscope to reduce the cross-sectional area of the endoscope of apparatus 10, which may enable apparatus 10 to maneuver along tortuous paths and access the target site. Elongated body 50 may be detachable from handle assembly 30 to facilitate insertion of elongated body 50 into a working channel of an endoscope or a channel of another device, for example by backloading elongated body 50 into the working channel. In some examples, elongated body 50 may be flexible, steerable, and/or may be rotatable about its axis. Elongated body 50 may include a lumen (or multiple lumens) for positioning actuation wires within (e.g., an actuation wire 52), for actuating end effector 100 via handle assembly 30 or actuating any other portion of apparatus 10. Elongated body 50 may be configured to receive a plurality of actuation wires or a single actuation wire. In some examples, elongated body 50 may be fixedly coupled to end effector 100, and in other examples elongated body 50 may be removably or releasably coupled to end effector 100. Unless stated otherwise, any wire or actuation device described herein may extend from handle assembly 30 to end effector 100 via a lumen of elongated body 50. Alternatively, or additionally, one or more of these actuation wires or devices may extend from handle assembly 30 to end effector 100 outside of (e.g., adjacent to) elongated body 50.

The endoscope assembly may include an endoscope handle (not shown) and a catheter 60 (e.g., a shaft) extending distally from a distal end of the endoscope handle. Catheter 60 may be the central shaft of a scope (e.g., a colonoscope, endoscope, duodenoscope, or the like). Catheter 60 may include one or more central lumens through which medical tools, imaging cables, and/or illumination cables may extend. The imaging cables and the illumination cables may connect to and may control imaging and light emitting devices, respectively, at a distal end of catheter 60. The medical tools may extend through one or more lumens of catheter 60 and may extend distally of a distalmost end of catheter 60. One or more medical tools may be used to grasp tissue at a target site and/or perform a medical procedure on tissue at the target site. For example, a grasper mechanism (such as a helical member having a pointed distal tip) may extend from the lumen at the distal end of catheter 60 and may grasp tissue by, e.g., skewering the tissue with the pointed distal tip and rotating the helical member. Other tools may also be extended from the distal end of catheter 60. The endoscope handle may include actuators, including knobs and/or buttons, to control the medical tools, imaging devices, and light emitting devices. Ports or other openings at the endoscope handle or at a proximal end of catheter 60 may provide access to the one or more lumens of catheter 60, and may allow the medical tools or other devices to be introduced into these lumens. Catheter 60 may also be connected, directly or via the endoscope handle, to an umbilicus, which may connect to a console and/or a display with which the user may interact to control image display, the light emitting devices, and/or other functions of the endoscope.

Handle assembly 30 may include a handle 32 and a body 34. Handle 32 may include a fixed portion 32a and an actuator portion 32b. Fixed portion 32a of handle 32 may be fixedly coupled to body 34. Actuator portion 32b may include a circular or oval portion or ring for positioning a user's finger within, which may assist a user in holding handle assembly 30. In some examples, actuator portion 32b of handle 32 may be an actuator which may be pivotally coupled to body 34 and movable relative to fixed portion 32a of handle 32. In some examples, actuator portion 32b of handle 32 may be coupled to a proximal portion of an actuation wire, such as an actuation wire 52, via an adjustable coupler 36, as will be described herein. In other examples, actuator portion 32b of handle 32 may be configured to control any other mechanism of apparatus 10, such as actuation of the deployment of staples from end effector 100 or the like via an actuation wire 52. It will be understood that actuation wire 52 may have sufficient rigidity to be pushed in the distal direction and pulled in the proximal direction.

In some examples, handle assembly 30 may include a moveable cover 38 pivotally coupled to housing 34 at pivot point 38b. In FIG. 1A, cover 38 is shown in an open position, exposing the internal portions of body 34. Cover 38 may be coupled to a proximal portion of body 34 and may cover the internal components of handle assembly 30 when positioned in a closed configuration, e.g., when a distalmost end 38a of cover 38 faces a surface 34a of body 34. Cover 38 may be positioned to cover the internal components of body 34 (e.g., a closed configuration) via a coupling mechanism at a distal portion of cover 38 and a distal portion of handle assembly 30, such as a snap-fit mechanism or the like. When in the closed configuration, cover 38 may form a pair of slots (not shown) in body 34. When the distal portion of cover 38 is uncoupled from the distal portion of body 34, a user may rotate or pivot cover 38 at pivot point 38b in order to access to the internal components of handle assembly 30.

Handle assembly 30 may include one or more adjustable couplers 36, 39, which may be configured to receive a portion of an actuation wire, such as actuation wire 52. Any of adjustable couplers 36, 39 may be a vice which is moveable in order to clamp down onto actuation wire 52 and fixedly couple actuation wire 52 to the adjustable couplers 36, 39. In some examples, adjustable couplers 36, 39 may be moveable via a screw to adjust couplers 36, 39 and couple or uncouple actuation wire 52 from couplers 36, 39. Couplers 36, 39 may be used in the movement of additional wires described herein.

Adjustable coupler 39 may be coupled to a longitudinal actuator 31 and moveable longitudinally via translating longitudinal actuator 31 within body 34. Longitudinal actuator 31 may be partially positioned within housing 34 and may be slidable longitudinally within the two slots formed when cover 38 is positioned over the internal components of handle assembly 30. Longitudinal actuator 31 may include a pair of opposing circular or oval portions or rings, with each circular portion defining an aperture for a user to position a respective finger within. In some examples, longitudinal actuator 31 may be coupled to an actuation wire (not shown), such as via adjustable coupler 39 or via a different coupler within body 34, and may be configured to control staple deployment from end effector 100. In other examples, longitudinal actuator 31 may be configured to control any other mechanism of apparatus 10, such as proximal/distal movement of actuation wire 52 or the like. Alternatively, two actuators may be used, a first actuator for actuating a cutting device and a second actuator for actuating a stapling device. It will be understood that handle assembly 30 is an example of an actuation device of end effector 100, and handle assemblies for actuating end effector 100 may be used.

End effector 100 may include a base unit 140 (FIGS. 1B and 1C) configured to receive a medical tool (such as a stapling device), or end effector 100 may include a pair of jaws, e.g., anvil 220 and a body 230 of a stapler device (FIGS. 2A and 2B), which may be coupled to the distal end of elongated body 50 via an attachment device 110. For example, base unit 140 may be a U-shaped member having a central slot 141 (FIG. 1D). Central slot 141 may be defined by a pair of walls 141a and a bottom wall to form a U-shaped base unit 140. Base unit 140 may be configured to receive the medical tool. The medical tool may be fixed within central slot 141 via an adhesive, a snap fit, laser welding, or other known attachment mechanism. The medical tool may be any tool for fixation, grasping, or the like. It will be understood that the medical tool may be removably attached to base unit 140 such that different medical tools may be used with base unit 140.

End effector 100 may include a pair of arms 142, 144 extending from a side of base unit 140. Each of the pair of arms 142, 144 may include an opening 142a, 144a, respectively, at an end of the pair of arms 142, 144 opposite an end attached to base unit 140. Each of openings 142a, 144a may receive a pin 118a, 118b, respectively, which may be pivotally fixed within openings 142a, 144a (FIG. 1E). A distal attachment device 114 (FIG. 1F) may be connected at the distal end of catheter 60 and may attach end effector 100 to catheter 60 (e.g., to the endoscope) about a pivot axis. For example, distal attachment device 114 may be a C-shaped member having openings 114a, 114b on radially opposite sides of distal attachment device 114. As shown in FIG. 1E, pins 118a, 118b may be received in and fixed to openings 114a, 114b, respectively, such that pins 118a, 188b define a pivot axis B. Distal attachment device 114 may be snap-fit onto a distal end of catheter 60 via the C-shaped configuration. Alternatively, distal attachment device 114 may be an annular ring and may receive catheter 60 through an opening in distal attachment device 114. Distal attachment device 114 may also be affixed using an adhesive, laser welding, or other known attachment mechanism, and the attachment mechanism may allow removal of distal attachment device 114. Elongate member 50 may be attached to a distal end of end effector 100, and may define a lumen through which one or more wires may extend for actuating end effector 100 and/or tools attached to end effector 100.

A proximal attachment device 112 is shown in FIG. 1G, and may be attached to catheter 60 proximal of distal attachment device 114 (e.g., FIG. 1B). Proximal attachment device 112 may include a first opening 112a, which may receive catheter 60, and a second opening 112b which may receive elongated member 50. Proximal attachment device 112 may be fixed to catheter 60 via an adhesive, laser welding, or other known attachment mechanism, and the attachment mechanism may allow removal of distal attachment device 114. Elongated member 50 may include a rigidity sufficient to receive a force in the proximal and distal directions to move an end effector as described herein.

With reference to FIGS. 1B and 1C, end effector 100 may be pivotally attached to catheter 60 via proximal attachment device 112 and distal attachment device 114. For example, proximal attachment device 112 may be attached before distal attachment device 114 to position proximal attachment device 112 proximally of distal attachment device 114. End effector 100 may be pivoted about axis B by relative movement of elongated member 50. For example, end effector 100 may be in a first orientation, e.g., an in-line orientation, where end effector 100 is approximately parallel to a longitudinal axis A of catheter 60 (FIG. 1C). Unless described otherwise, the first orientation of an end effector may provide a smaller cross-sectional area of apparatus 10 than a cross-section area of apparatus 10 when the end effector is in a second orientation (described herein). Distal movement of elongated member 50 may cause end effector 100 to move from the first orientation to a second orientation, in which a longitudinal axis E of end effector 100 forms an angle with longitudinal axis A of catheter 60 (FIG. 1B). For example, an angle formed between end effector 100 and longitudinal axis A may be approximately 0 degrees to approximately 90 degrees. It will be understood that this angle may be similar for all end effectors described herein, unless stated otherwise. In this manner, apparatus 10 may be introduced into the body with a smaller cross-sectional area, and end effector 100 may be rotated relative to catheter 60 to properly align end effector 100 with imaging devices, light emitting devices, and/or other tools supplied through catheter 60 at the target site.

A method of operating apparatus 10 having end effector 100 will now be described. Apparatus 10 may be introduced to a body via a natural orifice (e.g., the mouth or the anus) or via an incision or other medically-induced opening. End effector 100 may be advanced to a target site within the body via, e.g., by pushing distally on catheter 60 and/or elongated body 50. End effector 100 may be advanced along the catheter in a closed configuration, e.g., a configuration in which end effector 100 is parallel to longitudinal axis A of catheter 60, which may enable end effector 100 and catheter 60 to navigate one or more tortuous paths within the body.

Once end effector 100 reaches the target site within the body, the angle of end effector 100 relative to longitudinal axis A may be adjusted. For example, the user may move elongated body 50 in the distal direction, which may cause end effector 100 to rotate about pivot axis B. As the user moves elongated body 50 in the distal direction, the distal end of end effector 100 may move toward and/or may cross over longitudinal axis A, such that a middle portion of end effector 100 is positioned along longitudinal axis A (FIG. 1B). In some instances, a locking mechanism (not shown) provided at the distal end of catheter 60 and/or at handle assembly 30 may be activated to maintain a proper alignment of end effector 100 relative to longitudinal axis A.

Figure 2A:
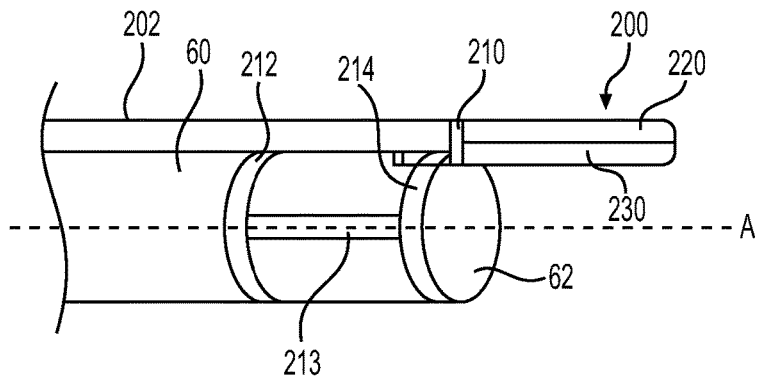
FIGS. 2A and 2B are side views of another exemplary end effector, according to an embodiment.

Once end effector 100 is properly positioned at the target site, the user may move actuation wire 52 in the proximal and the distal directions to actuate a medical tool (e.g., to pivot anvil 220 relative to body 230 as shown in FIG. 2A) to perform a medical procedure, such as grasp tissue, staple tissue, and/or perform other medical procedures to the tissue at the target site. The user may also use any tools, imaging devices, and/or light emitting devices associated with catheter 60. During the medical procedure, the user may change an angle of end effector 100 relative to longitudinal axis A.

Once the medical procedure is completed, apparatus 10 may be removed from the body. To remove apparatus 10, the user may pull elongated body 50 in the proximal direction (after unlocking a locking mechanism, if necessary), such that end effector 100 approaches the first orientation. Once end effector 100 achieves the first orientation, apparatus 10 may be removed from the body by pulling proximally on catheter 60. In some instances, a user may apply a force in the distal direction on elongated body 50 during removal of apparatus 10 to ensure end effector 100 maintains the first orientation. Alternatively, a locking mechanism may maintain the first orientation of end effector 100 during removal. In some instance, the medical tool attached to base 140 may be removed and another medical tool may be attached to base 140. Apparatus 10 may be reintroduced to the body (via a same or a different body opening) and one or more additional medical procedures may be performed. In this manner, end effector 100 including base 140 may include interchangeable tools to perform multiple procedures with a single apparatus 10.

Figure 2B:
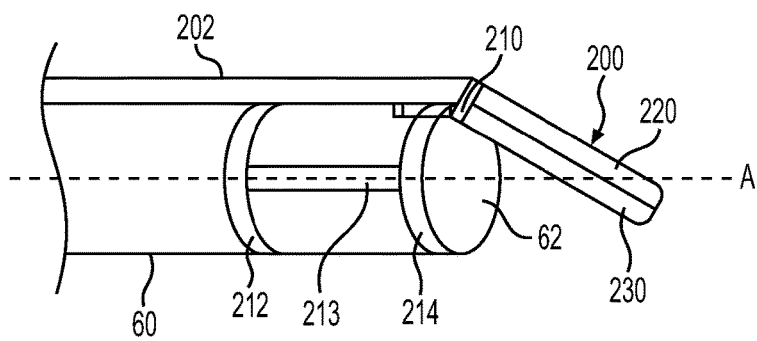

FIGS. 2A and 2B illustrate another example of an end effector 200. As described herein, end effector 200 may include a pair of jaws, e.g., an anvil 220 and a body 230, pivotally connected to each other. Similar to end effector 100, end effector 200 may include a mechanism for connecting end effector 200 to the distal end of catheter 60. For example, a proximal attachment mechanism 212 and a distal attachment mechanism 214 may be attached to catheter 60 via a snap-fit, an adhesive, laser welding, or other known attachment means. In one example, proximal and distal attachment mechanisms 212, 214 are connected via a band 213, which may support in connecting proximal and distal attachment mechanisms 212, 214 to catheter 60 and/or may maintain an orientation of proximal and distal attachment mechanisms 212, 214 relative to each other. Proximal and distal attachment mechanisms 212, 214 may have the same shape or a different shape, and may be annular rings with an opening, or may be C-shaped.

A hinge 210 defining a pivot axis may connect end effector 200 to distal attachment mechanism 214. Hinge 210 may enable end effector to rotate from the first orientation where a longitudinal axis of end effector 200 is parallel to longitudinal axis A in FIG. 2A (the in-line orientation), to a second orientation (FIG. 2B) in which the longitudinal axis of end effector 200 is angled relative to longitudinal axis A. A wire 202 may extend from end effector 200 in a proximal direction and may be actuated by a user and/or by an actuator associated with handle assembly 30. Wire 202 may extend on an outer surface of catheter 60 and may have a rigidity sufficient to move end effector 200 about hinge 210 and, in some cases, provide a rigidity sufficient to maintain a position of end effector 200 about hinge 210. Wire 202 may be moved in a distal direction to move end effector 200 from the first orientation to the second orientation, and wire 202 may be moved in the proximal direction to move end effector 200 from the second orientation to the first orientation. While not shown in FIGS. 2A and 2B, elongate member 50 may extend from end effector 200 in the distal direction and on the outer surface of catheter 60. As described herein, actuation wire 52 may extend from handle assembly 30 to end effector 200 via the lumen of elongated member 50. It will be understood that a locking mechanism (not shown) may be used to maintain a position of end effector 200 in the first orientation, the second orientation, or both.

A method of operating apparatus 10 having end effector 200 will now be described. Apparatus 10 may be introduced to a body and advanced to a target site as described herein. End effector 200 may be advanced in the first configuration, which may enable end effector 200 and catheter 60 to navigate one or more tortuous paths within the body.

Once end effector 200 reaches the target site within the body, the angle of end effector 200 relative to longitudinal axis A may be adjusted. For example, the user may move actuation wire 202 in the distal direction, which may cause end effector 200 to rotate about hinge 210. As the user moves actuation wire 202 in the distal direction, the distal end of end effector 200 may move toward and/or may cross over longitudinal axis A, such that a middle portion of end effector 200 is positioned along longitudinal axis A (FIG. 2B). In some instances, a locking mechanism (not shown) provided at the distal end of catheter 60 and/or at handle assembly 30 may be activated to maintain a proper alignment of end effector 200 relative to longitudinal axis A.

Once end effector 200 is properly positioned at the target site, the user may move actuation wire 52 in the proximal and the distal directions to actuate anvil 220 relative to body 230 to perform a medical procedure, such as grasp tissue, staple tissue, and/or perform other medical procedures to the tissue at the target site. The user may also use any tools, imaging devices, and/or light emitting devices associated with catheter 60. During the medical procedure, the user may change an angle of end effector 200 relative to longitudinal axis A.

Once the medical procedure is completed, apparatus 10 may be removed from the body. To remove apparatus 10, the user may pull actuation wire 202 in the proximal direction, causing end effector 200 to rotate about hinge 210 into the first orientation. Once end effector 200 achieves the first orientation, apparatus 10 may be removed from the body as described herein.

FIGS. 3A-3D illustrate another example of an end effector 300. As described herein, end effector 300 may include a pair of pivotally connected jaws and may be any grasping, cutting, stapling, or similar medical tool. As described herein, elongated member 50 may be attached to a distal end of end effector 300 and may extend proximally to handle assembly 30. End effector 300 is connected to a distal end of an arm 310 by a pin 318 via openings (not shown) in each of end effector 300 arm 310. Pin 318 defines a pivot axis about which end effector 300 may pivot relative to arm 310. A second pin 312 is connected to catheter 60 and attached to a second opening (not shown) in a proximal end of arm 310. Second pin 312 is located in a pocket 330 of catheter 60, which may be defined by walls 332. Walls 332 may extend radially outward from an outer surface of catheter 60, or may extend radially inward (e.g., toward longitudinal axis A of catheter 60) from an inner wall defining a lumen of catheter 60. Second pin 312 may define a second pivot point about which arm 310 may pivot.

Figure 3A:
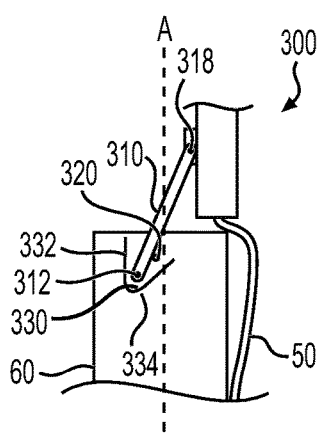
FIGS. 3A, 3B, and 3C are side views of another exemplary end effector, according to an embodiment.
Figure 3B:
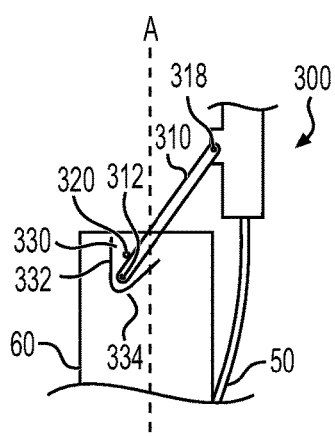
Figure 3C:
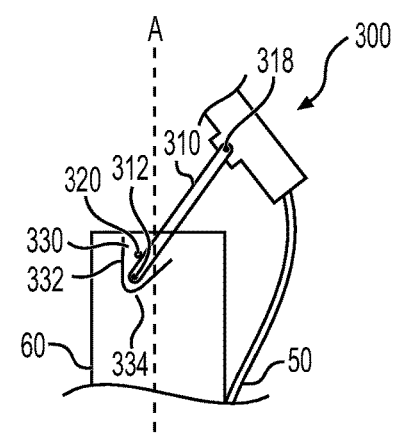
Figure 3D:
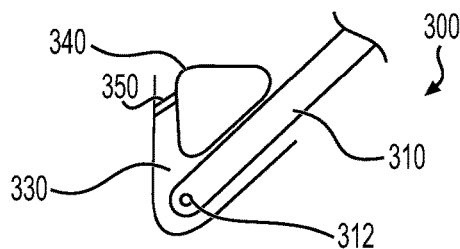
FIG. 3D is a side view of a control mechanism of the end effector of FIGS. 3A-3C, according to an embodiment.

A protrusion 320 may extend from a surface of catheter 60 into pocket 330. Protrusion 320 may be a bump, e.g., a rounded bump, which may prevent pivotal movement of arm 310 within pocket 330 absent a force. For example, arm 310 may be in a first position, e.g., on a left side of protrusion 320 in FIG. 3A, which may cause end effector 300 to be in the first orientation. A force sufficient to move arm 310 over protrusion 320 may be supplied by elongated member 50, e.g., by moving elongated member 50 in a proximal direction. When this force is supplied, arm 310 move from the first position to a second position, such that arm 310 is positioned on the right side of pocket 330 (FIG. 3B). As arm 330 moves to the second position, end effector 300 may move radially outward, enabling end effector to rotate about the pivot axis defined by pin 318. Once arm 330 is in the second position, a user may move elongated member 50 in the proximal and distal directions to cause end effector to pivot about the pivot axis defined by pin 318, thereby enabling end effector 300 to form a desired angle with longitudinal axis A.

Alternatively, arm 310 may be rotated about the pivot axis defined by pin 312 by inflating or deflating a fluid container 340. For example, fluid (e.g., saline, air, or other fluid) may be supplied to fluid container 340 via a fluid lumen 350. When there is no fluid present in fluid container 340, arm 310 may be in the first position, and when fluid is supplied to fluid container 340, arm 310 may rotate to the second position, enabling end effector 300 freedom to be angled relative to longitudinal axis A.

A method of operating apparatus 10 having end effector 300 will now be described. Apparatus 10 may be introduced to a body and advanced to a target site as described herein. End effector 300 may be advanced in the first configuration, which may enable end effector 300 and catheter 60 to navigate one or more tortuous paths within the body.

Once end effector 300 reaches the target site within the body, the user may move elongated member 50 in a proximal direction with a force sufficient to overcome the force provided by protrusion 320 to move arm 310 from the first position (FIG. 3A) to the second position (FIG. 3B). Alternatively, a fluid may be supplied via fluid lumen 350 to fluid container 340 to move arm 310 from the first position to the second position.

Once arm 310 is positioned in the second position, the user may move elongated member 50 in the distal and proximal directions to pivot end effector 300 about pin 318 to a desired angle relative to longitudinal axis A. A locking mechanism (not shown) may be activated to maintain the desired position of end effector 300. The user may actuate jaws of end effector 300 via actuation wire 52, as described herein. Once the medical procedure is complete, the user may move elongated member 50 distally with sufficient force to move arm 310 from the second position to the first position, thereby locking end effector 300 in the first orientation. Alternatively, arm 310 may be moved from the second position to the first position by removing fluid from fluid container 340 via fluid lumen 350. Once end effector 300 achieves the first orientation, apparatus 10 may be removed from the body as described herein.

An end effector 400 according to another example is shown in FIG. 4B. End effector 400 may include a pair of pivotally connected jaws, such as an anvil 420 and a body (not shown), and may be used to grasp, cut, staple, or perform other medical procedures on the tissue. Elongated member 50 may extend proximally from a distal end of end effector 400. End effector 400 may be attached to catheter 60 via a proximal attachment device 402 and a distal attachment device 404. Proximal and distal attachment devices 402, 404 may be attached to catheter 60 in any manner described herein. For example, proximal and distal attachment devices 402, 404 may include lumens defined by an inner wall. The inner wall of the lumens of proximal and distal attachment devices 402, 404 may have a diameter larger than a diameter of an outer surface of catheter 60, such that proximal and distal attachment devices 402, 404 may slide onto catheter 60 and may be fixed to catheter 60 via, example, an adhesive, laser welding, or the like.

A proximal link 410 and a distal link 412 may connect end effector 400 to distal attachment device 404. For example, a proximal end of proximal link 410 may be pivotally connected to distal attachment device 404 via a pin 414a. Pin 414b may connect a distal end of proximal link 410 to a proximal end of distal link 412. A pin 414c may connect a distal end of distal link 412 to an extension member 422 of end effector 400. Each of pins 414a, 414b, 414c defines a pivot axis about which links 410, 412, and end effector 400 may be pivoted. For example, end effector 400 may be moved from the first orientation (approximately parallel to longitudinal axis A) to the second orientation, in which end effector 400 is angled relative to longitudinal axis A. For example, proximal movement of elongated member 50 may cause links 410, 412 and end effector 400 to move proximally, which may cause end effector to pivot about the pivot axis defined by pin 414c. A locking mechanism (not shown) may be provided at end effector 400 and/or handle assembly 30 to prevent movement of elongated member 50, thereby locking an orientation of end effector 400.

A method of operating apparatus 10 having end effector 400 will now be described. Apparatus 10 may be introduced to a body and advanced to a target site as described herein. End effector 400 may be advanced in the first configuration, which may enable end effector 400 and catheter 60 to navigate one or more tortuous paths within the body.

Once end effector 400 reaches the target site within the body, the user may move elongated member 50 in a proximal direction, which may cause end effector 400 and links 410, 412 to move radially outward and proximally, moving end effector into the second orientation. Once end effector 400 is in the second orientation, the user may actuate jaws of end effector via actuation wire 52, as described herein. Once the medical procedure is complete, the user may move elongated member 50 distally to push end effector 400 and links 410, 412 in the distal direction and into the first orientation. Once end effector 400 achieves the first orientation, apparatus 10 may be removed from the body as described herein.

An end effector 500 according to another embodiment is illustrated in FIGS. 5A and 5B. End effector 500 may be similar to the other end effectors already described herein, and may include a pair of pivotally connected jaws (e.g., anvil 520 and base 530). A proximal end of end effector 500 may be attached to an extension member 518 (in some instances, extension member 518 may be attached to end effector 500 via a pivot axis 518a). Extension member 518 may be attached at its proximal end to a wire 502 which may extend proximally to handle assembly 30. Wire 502 may extend through an annular ring 516, or other similar device, attached to a side of a distal end portion of catheter 60.

A first orientation of end effector 500 is shown in FIG. 5A, in which extension member 518 is located distally of a distalmost end of annular device 516. In this manner, end effector 500 may extend distally of a distalmost end of catheter 60 during an insertion of catheter 60 to a target site. A second orientation of end effector 500 is shown in FIG. 5B. In the second orientation, a portion of extension member 518 extends proximally through an opening of annular device 516. The second orientation may allow end effector 500 to pivot about pivot axis 518a, enabling end effector 500 to be angled relative to longitudinal axis A. In this manner, a user may move elongate member 50 (not shown in FIGS. 5A and 5B, but connected to a proximal end of end effector 500 as described herein) to rotate end effector 500 about pivot axis 518a.

A method of operating apparatus 10 having end effector 500 will now be described. Apparatus 10 may be introduced to a body and advanced to a target site as described herein. End effector 500 may be advanced in the first configuration, in which end effector 500 is located distally of distal end 514 of catheter 60. During insertion, distal end 514 may push end effector 500 toward the target site, which may enable end effector 500 and catheter 60 to navigate one or more tortuous paths within the body.

Once end effector 500 reaches the target site within the body, the user may move wire 502 in a proximal direction, which may cause end effector 500 and extension member 518 to also move in a proximal direction. Once a portion of extension member 518 is disposed within the opening of annular device 516, the user may move and elongated member (not shown) (e.g., elongated member 50) to change an angle of a longitudinal axis end effector 500 relative to longitudinal axis A and/or may actuate jaws of end effector via actuation wire 52, as described herein. For example, the elongated member may be moved in the proximal and distal directions and may cause end effector 500 to rotate about pivot axis 518a. Once the medical procedure is complete, the user may move wire 502 distally to push end effector 500 in the distal direction and disconnect extension member 518 from annular device 516. Once end effector 500 achieves the first orientation, apparatus 10 may be removed from the body as described herein. Proximal movement of catheter 60 may move end effector 500 proximally from the target site and from the body.

An end effector 600 according to another example is shown with reference to FIGS. 6A and 6B. End effector 600 includes a pair of jaws, e.g., an anvil 620 and a base 630, connected by links to an end cap 614. End cap 614 is attached to a distal end of catheter 60 via an adhesive, laser welding, snap fit, screw threads, or other known connection.

End effector 600 is attached via a pair of distal links 610a, 610b and a pair of proximal links 604a, 604b. A first end of distal link 610a is attached to a distal pin 620b on anvil 620, while a first end of distal link 610b is attached to a distal pin 630b on body 630. Opposite ends of first and second distal links 610a, 610b are joined together by a pin 612. Pins 620b, 630b, and 612 each define a pivot axis, such that distal links 610a and 610b may pivot relative to anvil 620, body 630, and each other.

Similarly, a first end of proximal link 604a is attached to a proximal pin 620a of anvil 620, and a first end of proximal link 604b is attached to a proximal pin 630a of body 630. Opposite ends of each of proximal links 604a, 604b are attached to a wire 602 via openings 608a, 608b, respectively. Proximal links 604a, 604b are pivotally attached together via pin 606. Pins 620a, 630a, and 606 each define a pivot axis, such that proximal links 604a and 604b may pivot relative to anvil 620, body 630, and each other.

Anvil 620 and body 630 are in a first orientation in FIG. 6A. The first orientation provides a smaller cross sectional area of end effector 600, which may improve the ability of assembly 10 to navigate a tortuous path. In this first orientation, anvil 620 is positioned on a first side of longitudinal axis A, and body 630 is positioned on a second side of longitudinal axis A, opposite anvil 620. A distal movement of wire 602 may cause proximal links 604a, 604b and distal links 610a, 610b to rotate, thereby moving anvil 620 and body 630 radially outward away from longitudinal axis A and in a proximal direction. It will be understood that a spring (not shown) may assist a movement of anvil 620 and body 630 radially outward from longitudinal axis A and in the proximal direction. In this second orientation, tissue or other material may be placed between anvil 620 and body 630, and/or tools, imaging devices, and/or light emitting devices may be extended from a lumen of catheter 60. A proximal movement of wire 602 may cause links 604a, 604b and 610a, 610b to cause anvil 620 and body 630 to move distally and rotate back toward longitudinal axis A and into the first orientation. In this manner, a user may grasp, staple, cut, or perform additional medical procedures on tissue. In some instances, elongated member 50 may extend a portion or an entirety of wire 602 and may contain wire 602 within a lumen of elongated member 50. This may protect wire 602 during use.

A method of operating apparatus 10 having end effector 600 will now be described. Apparatus 10 may be introduced to a body and advanced to a target site as described herein. End effector 600 may be advanced in the first configuration, in which anvil 620 and body 630 are oriented along longitudinal axis A. Once end effector 600 reaches the target site within the body, the user may move wire 602 in a distal direction, which may cause anvil 620 and body 630 to move proximally and radially outward. The user may advance end effector 600 to grasp tissue or other matter at the target site by additionally moving wire 602 in the distal direction. End effector 600 may be moved from the first orientation to the second orientation multiple times during a medical procedure. Once the medical procedure is complete, the user may move wire 602 proximally to return end effector 600 to the first orientation and apparatus 10 may be removed from the body as described herein.

Figure 7B:
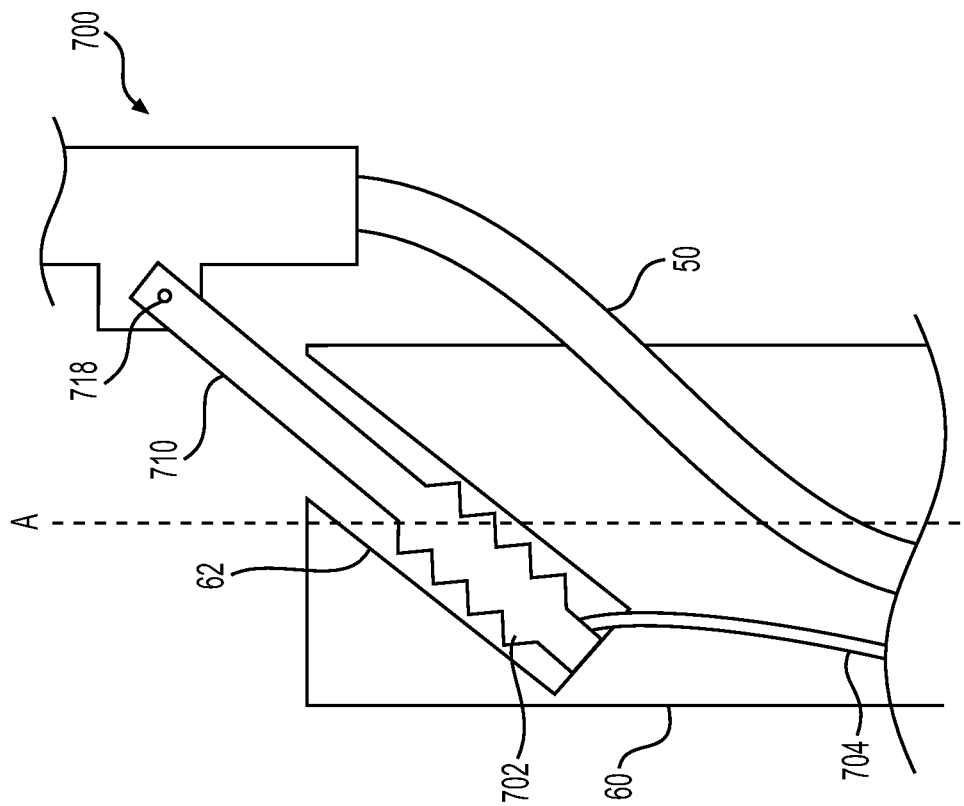
FIGS. 7A and 7B are side views of another exemplary end effector, according to an embodiment.
Figure 7A:
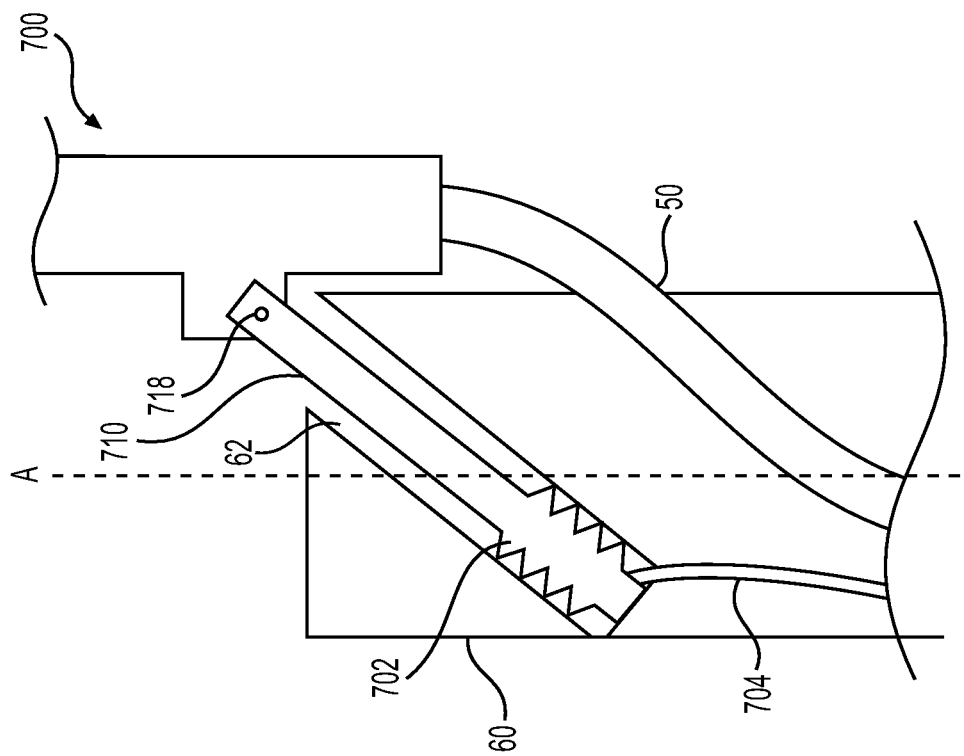

FIGS. 7A and 7B illustrate another example of an end effector 700. As described herein, end effector 700 may include a pair of jaws pivotally connected to each other. A pin 718 may connect a distal end of an arm 710 to end effector 700. Pin 718 may define a pivot axis. Arm 710 may extend within a cavity 62 defined within a sidewall of a distal end of catheter 60. Cavity 62 may be angled relative to longitudinal axis A. A proximal end of arm 710 may include, or may be connected to, a fluid container 702. Fluid container 702 may be connected to a fluid lumen 704, which may supply fluid from a proximal end of apparatus 10 to fluid container 702.

Supplying fluid to fluid container 702 may cause arm 710 to move from a first position shown in FIG. 7A, to a second, extended position in FIG. 7B. For example, fluid container 702 may include baffles or some other configuration that, when not supplied with fluid, positions arm 710 almost entirely within cavity 62. When fluid is supplied to fluid container 702, the baffles expand and arm 710 extends from a distal end of cavity 62 to a second position. This distal movement enables end effector 700 to pivot about the pivot axis defined by pin 718. In this manner, distal and proximal movement of elongated member 50 attached to end effector 700 may cause end effector 700 to move from the first orientation, in which end effector 700 is approximately parallel to longitudinal axis A, to the second orientation, where end effector 700 is angled relative to longitudinal axis A.

A method of operating apparatus 10 having end effector 700 will now be described. Apparatus 10 may be introduced to a body and advanced to a target site as described herein. End effector 700 may be advanced in the first configuration, which may enable end effector 700 and catheter 60 to navigate one or more tortuous paths within the body.

Once end effector 700 reaches the target site within the body, a user may supply fluid to fluid container 702 via fluid lumen 704, thereby moving a portion of arm 710 in the distal direction, and out of cavity 62. Subsequently, the user may move elongated body 50 in the distal direction, which may cause end effector 700 to rotate about the pivot axis defined by pin 718. As the user moves elongated body 50 in the distal direction, the distal end of end effector 700 may move toward and/or may cross over longitudinal axis A as described herein. In some instances, a locking mechanism (not shown) provided at the distal end of catheter 60 and/or at handle assembly 30 may be activated to maintain a proper alignment of end effector 700 relative to longitudinal axis A.

Once end effector 700 is properly oriented at the target site, the user may move actuation wire 52 in the proximal and the distal directions to actuate the pair of jaws of end effector 700 to perform one or more medical procedures to the tissue at the target site.

Once the medical procedure is completed, apparatus 10 may be removed from the body. To remove apparatus 10, the user may move elongated member 50 in the proximal direction to align end effector 700 in the first orientation. The user may remove the fluid supply from fluid container 702, which may cause the baffles to collapse and move the portion of arm 710 into cavity 62, locking end effector 700 in the first orientation. Once end effector 700 achieves the first orientation, apparatus 10 may be removed from the body as described herein.

Figure 8C:
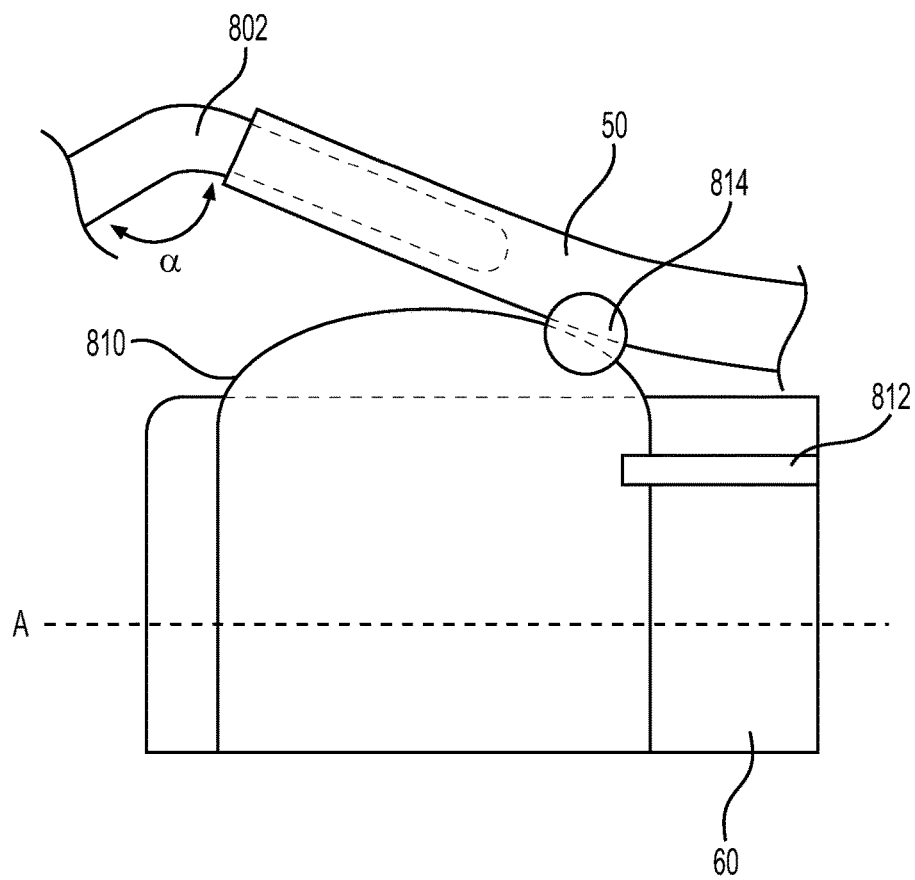

An end effector according to another example is shown in FIGS. 8A-8D. End effector 800 may be any end effector described herein and may be connected to elongated member 50 via an attachment member 802 having an angled portion defined by an angle α. A fluid container 810 (e.g., a fluid balloon) may be disposed on at a distal end and on an outer surface of catheter 60. A first side of fluid container 810 may contact catheter 60 and an opposite side of fluid container 810 may contact elongated member 50 and/or attachment member 802. Fluid may be supplied to fluid container 810 via a fluid lumen 812 to move end effector 800 from the first orientation (FIG. 8A) to the second orientation (FIG. 8B). The angle α may be set such that, when fluid container 810 contains a fluid, end effector 800 may be properly oriented in the second orientation to perform a medical procedure. For example, angle α may range from approximately 180 degrees, e.g., such that end effector 800 is approximately parallel to longitudinal axis A, to approximately 90 degrees. It will be understood that during insertion to the target site, end effector 800 may pivot freely such that angle α may extend past 180 degrees, i.e., greater than 180 degrees. For example, a material of attachment member 802 may allow for this freedom of movement. In this manner, end effector 800 may conform to the body or a body lumen during insertion.

Figure 8D:
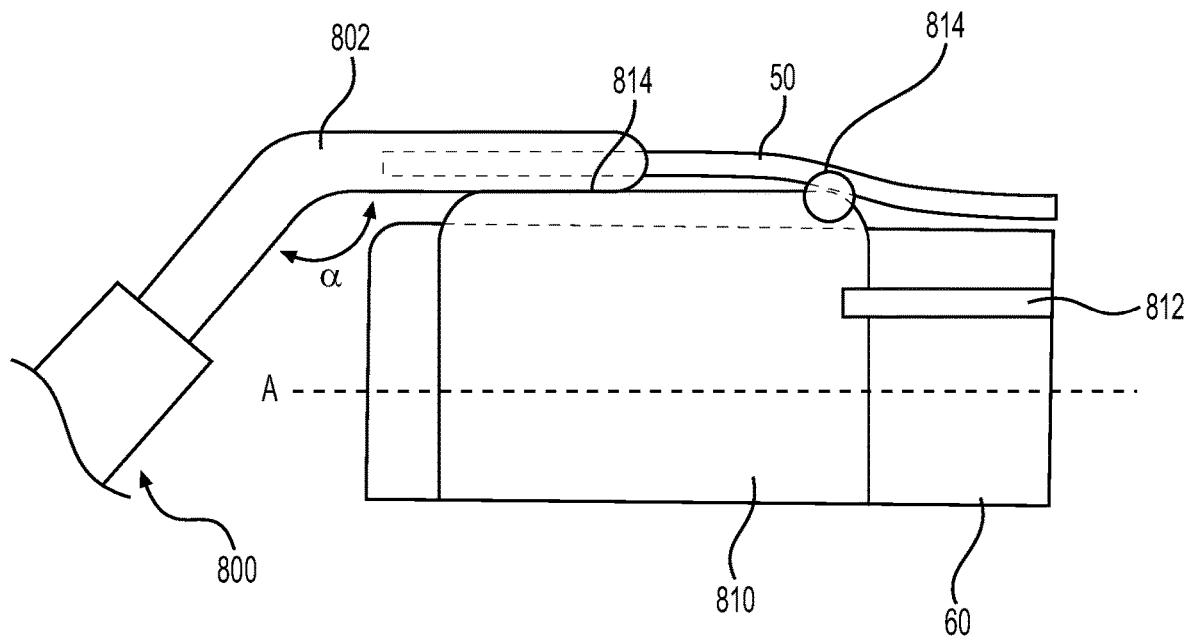

In certain instances, elongated member 50 and/or attachment member 802 may be connected to fluid container 810 via an attachment mechanism 814 (FIGS. 8C and 8D), such as an adhesive or the like. In some examples, attachment member 802 may have an outer diameter less than an inner diameter of a lumen of elongated member 50. In this manner, attachment member 802 may be attached within the lumen of elongated member 50 (FIGS. 8A-8C). Alternatively, an outer diameter of elongated member 50 may be less than an inner diameter of a lumen of attachment member 802. In this manner, elongated member 50 may be attached within the lumen of attachment mechanism 802 (FIG. 8D).

A method of operating apparatus 10 having end effector 800 will now be described. Apparatus 10 may be introduced to a body and advanced to a target site as described herein. End effector 800 may be advanced in the first configuration, which may enable end effector 800 and catheter 60 to navigate one or more tortuous paths within the body.

Once end effector 800 reaches the target site within the body, a user may supply fluid to fluid container 810 via fluid lumen 812, thereby moving elongated body 50 and/or attachment member 802 radially outward. Once end effector 800 is properly oriented at the target site, the user may move actuation wire 52 in the proximal and the distal directions to actuate the pair of jaws of end effector 800 to perform one or more medical procedures to the tissue at the target site.

Once the medical procedure is completed, apparatus 10 may be removed from the body. To remove apparatus 10, the user may remove the fluid supply from fluid container 810, which may cause elongated member 50 and/or attachment member 802 radially inward to longitudinal axis A. Once end effector 800 achieves the first orientation, apparatus 10 may be removed from the body as described herein. It will be understood that attachment member 802 may have flexibility such that angle α may change during removal of apparatus 10 such that end effector 800 can follow the contours of the body lumen.

Figure 9A:
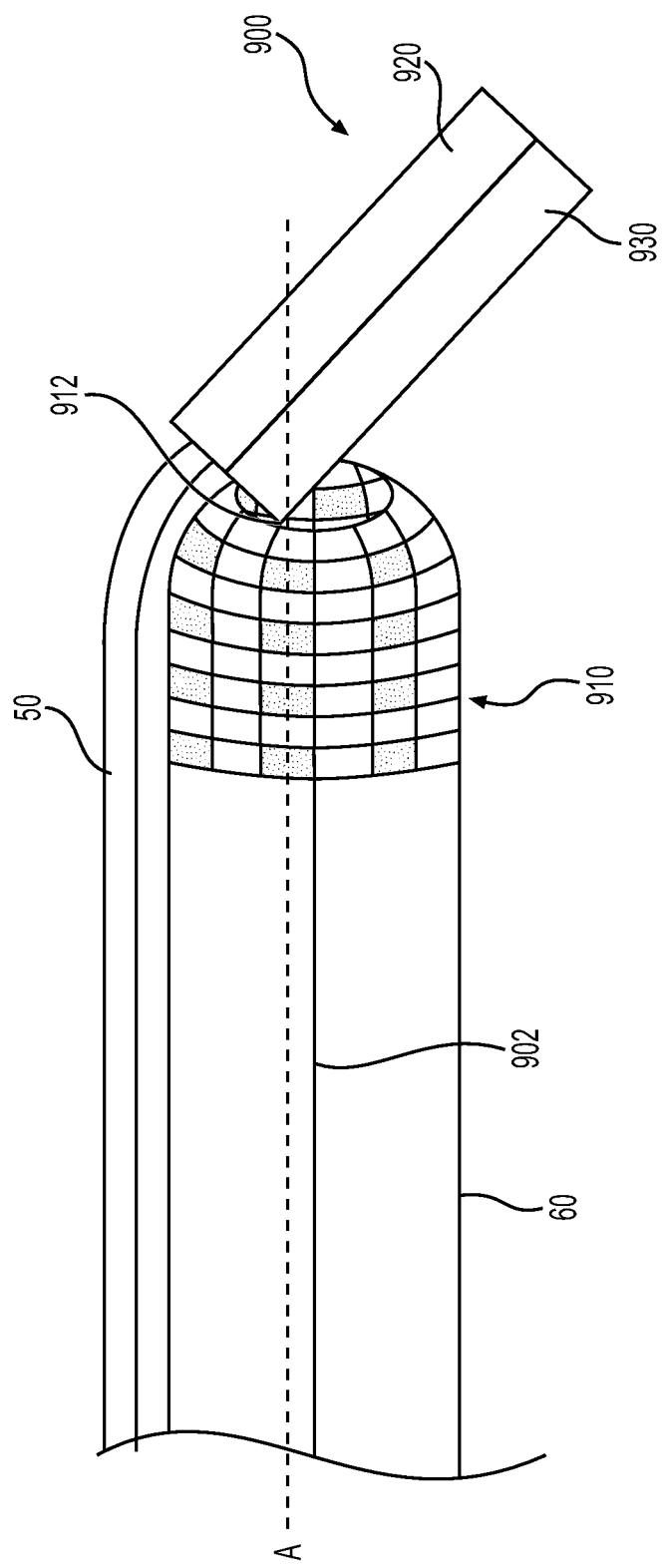
FIGS. 9A and 9B are side views of a still further exemplary end effector, according to an embodiment.
Figure 9B:
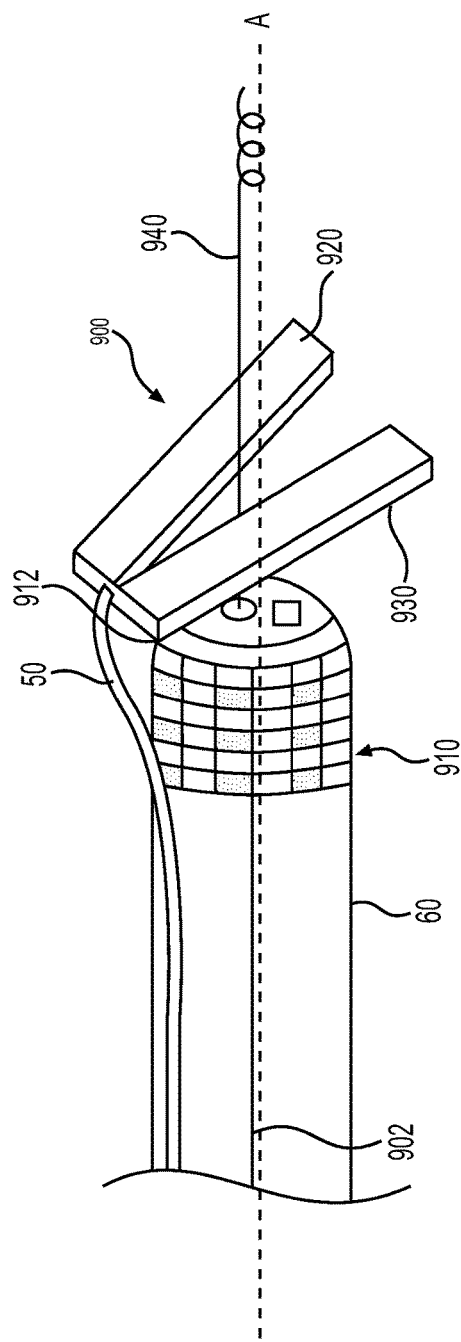

An end effector 900 including an anvil and a body 930 are illustrated in FIGS. 9A and 9B. Elongate member 50 may extend from end effector 900 to a proximal end of catheter 60. While not shown, actuation wire 52 may be attached to and extend through a lumen of elongate member 50 to control relative movement of anvil 920 and body 930 to each other. End effector 900 may be connected to a sleeve 910 via a connection point 912 using an adhesive, a laser welding, a pivotal connection mechanism, or any other known connection mechanism. As shown in FIGS. 9A and 9B, a wire 902 extends from sleeve 910 in a proximal direction and may be actuated to move sleeve 910 in a proximal or a distal direction, as described herein.

Figure 9C:
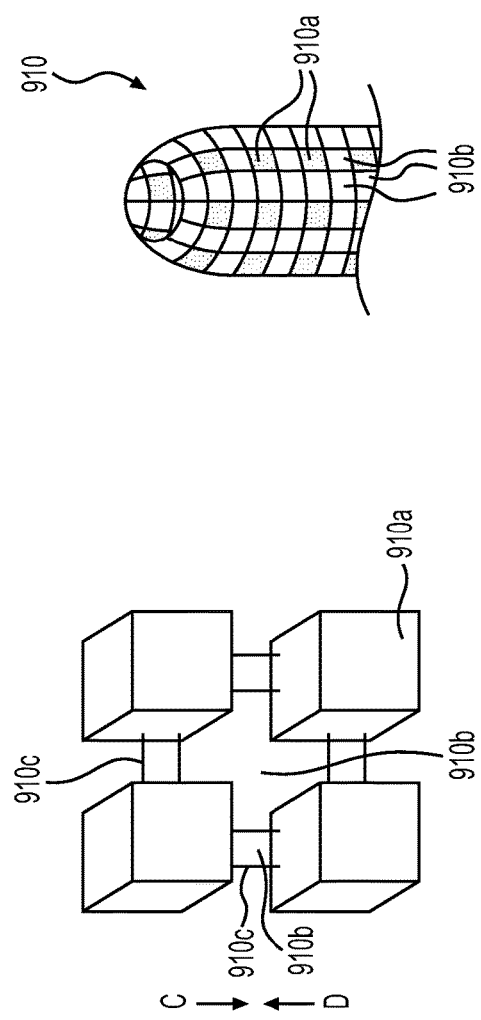
FIG. 9C is a side view of an attachment mechanism of the end effector of FIGS. 9A and 9B, according to an embodiment.

Sleeve 910 is shown in detail in FIG. 9C. Sleeve 910 includes a plurality of members 910a connected together by a plurality of elastic members 910c. When in an expanded configuration, spaces 910b may be defined between members 910a. Members 910a may include any material suitable for use in a medical procedure, such as a polymer or similar material suitable for use in the body. Elastic members 910c may urge adjacent members 910a towards each other, as shown by arrows C and D in FIG. 9C. For example, a portion of sleeve 910 may be attached to catheter 60 and a portion of sleeve 910 may be distal a distalmost end of catheter 60 (FIG. 9A). In this instance, sleeve 910 may be stretched such that an inner surface of sleeve 910 fits over and contacts an outer surface of catheter 60. The portion of the sleeve disposed on catheter 60 is stretched such that spaces 910b are formed between adjacent members 910a. In contrast, elastic members 910c may contract in the portion of sleeve 910 that is distal the distalmost end of catheter 60, causing adjacent members 910a to move closer together, such that spaces 910b between adjacent members 910a become smaller or disappear. This contraction of sleeve 910 may cause end effector 900 to be in a first orientation and be movable relative to catheter 60 during insertion into a body. For example, end effector 900 may not be rigidly fixed to catheter 60, such that end effector 900 may be in this first position and may move and navigate tortuous paths within the body.

Referring to FIG. 9B, sleeve 910 is in a second position in which a distal end of sleeve 910 is proximal of or flush with a distalmost end of catheter 60. The user may move wire 902 in a proximal direction to move sleeve 910 from the first position to the second position. In this manner, end effector 900 may be positioned in a second orientation, e.g., angled relative to longitudinal axis A, such that end effector 900 may perform a medical procedure. End effector 900 may be supported on catheter 60 by sleeve 910 such that end effector 900 maintains the first orientation during the medical procedure. Distal movement of wire 902 may move sleeve 910 from the second position to the first position. A stop, such as an annular raised portion, may prevent movement of sleeve 910 off of a distalmost end of catheter 60. It will be understood that a force provided by elastic members 910c may be sufficient to support end effector 900 on catheter 60 during insertion to the target site and during a medical procedure.

A method of operating apparatus 10 having end effector 900 will now be described. Apparatus 10 may be introduced to a body and advanced to a target site as described herein. End effector 900 may be advanced in the first configuration, in which sleeve 910 is in the first position, e.g., a portion of sleeve 910 is distal of the distalmost end of catheter 60. This may enable end effector 900 and catheter 60 to navigate one or more tortuous paths within the body.

Once end effector 900 reaches the target site within the body, a user may move wire 902 in the proximal direction, thereby moving sleeve 910 proximally such that the distal end of sleeve 910 is distal or flush with the distalmost end of catheter 60, positioning end effector in the second orientation. Once end effector 900 is properly oriented at the target site, the user may move actuation wire 52 in the proximal and the distal directions to actuate the pair of jaws of end effector 900 to perform one or more medical procedures to the tissue at the target site.

Once the medical procedure is completed, apparatus 10 may be removed from the body. To remove apparatus 10, the user may move wire 902 in the distal direction to move the distal end of sleeve 910 distal of the distalmost end of catheter 60, such that end effector 900 is moved to the first orientation. Once end effector 900 achieves the first orientation, apparatus 10 may be removed from the body as described herein.

While exemplary medical systems have been described, it will be understood that the particular arrangements of elements in these fastening systems are not limited. Moreover, a size, a shape, and/or the materials of the fastening systems are not limited. As described herein, there is included a control mechanism for controlling an orientation of an end effector relative to a longitudinal axis of a scope. Performing various medical procedures may be improved by enabling a user to insert the end effector in a first orientation to reduce a size of the device and to move to the end effector to a second orientation to enable the end effector to perform one or more medical operations using the end effector.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a shaft including a longitudinal axis;
   an end effector connected to a distal end of the shaft and configured to move from a first orientation, where a longitudinal axis of the end effector is approximately parallel to the longitudinal axis of the shaft, to a second orientation, where an angle is formed between the longitudinal axis of the end effector and the longitudinal axis of the shaft, wherein the end effector includes a U-shaped body portion configured to receive a medical tool, wherein the U-shaped body portion comprises a pair of walls and a bottom wall, wherein the U-shaped body portion includes a pair of arms extending from one of the pair of walls;
   an elongated member attached to a proximal end of the end effector, wherein manipulation of the elongated member is configured to move the end effector between the first orientation and the second orientation; and
   a fixation device configured to be connected to a distal end of the shaft, wherein the end effector is pivotally coupled to the fixation device via a pair of pins, wherein the pair of pins defines an axis about which the end effector is configured to rotate, and wherein each pin of the pair of pins is received by a respective opening of each arm of the pair of arms.

2. The medical device of claim 1, wherein the fixation device is a first fixation device, and wherein the medical device further comprises:
   a second fixation device configured to be connected to the shaft proximal of the first fixation device.

3. The medical device of claim 2, wherein the second fixation device includes an opening configured to receive the medical tool.

4. The medical device of claim 3, wherein the opening in the second fixation device is a first opening, and wherein the second fixation device further includes a second opening configured to receive the elongated member.

5. The medical device of claim 1, wherein movement of the elongated member in a distal direction is configured to move the end effector from the first orientation to the second orientation.

6. The medical device of claim 1, wherein the fixation device includes a C-shaped member.

7. The medical device of claim 6, wherein the C-shaped member includes a pair of openings, each of the pair of openings configured to accept a pin of the pair of pins.

8. The medical device of claim 7, wherein the pair of openings are positioned on radially opposite sides of the C-shaped member.

9. The medical device of claim 6, wherein the C-shaped member is removably coupled to the medical tool.

* * * * *